United States Patent [19]
Schierjott et al.

[11] 3,930,798
[45] Jan. 6, 1976

[54] METHOD AND APPARATUS FOR TESTING AQUEOUS SAMPLES

[76] Inventors: Günter Schierjott, Tm Haarmannsbusch 1, 463 Bochum, Germany; Herbert A. Bleier, Barawitzkagasse 27/1/536, A-1190 Vienna, Austria

[22] Filed: May 9, 1973

[21] Appl. No.: 358,833

[52] U.S. Cl. .............................. 23/230 R; 23/253 R
[51] Int. Cl.² .......................................... G01N 33/18
[58] Field of Search ........ 23/230 R, 253 R, 230 PC, 23/253 PC

[56] References Cited
UNITED STATES PATENTS

| | | | |
|---|---|---|---|
| 3,512,936 | 5/1970 | Clements | 23/230 R |
| 3,540,845 | 11/1970 | Overbeck et al. | 23/230 R |
| 3,703,355 | 11/1972 | Takahashi et al. | 23/230 PC |

FOREIGN PATENTS OR APPLICATIONS

| | | |
|---|---|---|
| 2,243,461 | 3/1973 | Germany |

OTHER PUBLICATIONS

Chem. Abstr., Vol. 73:80310w (1970).
Chem. Abstr., Vol. 73:80353n (1970).
Chem. Abstr., Vol. 78:151508h (1973).

*Primary Examiner*—Morris O. Wolk
*Assistant Examiner*—Timothy W. Hagan
*Attorney, Agent, or Firm*—Hubbell, Cohen, & Stiefel

[57] ABSTRACT

Method and apparatus for simultaneously and continuously determining the total inorganic carbon, total organic carbon (TOC) and chemical oxygen demand (COD) of an aqueous sample. The method involves first converting all inorganic carbon to $CO_2$, the amount of which is determined. The organic carbon is converted, by treatment with an excess of an oxidizing agent, into $CO_2$, which is conductimetrically determined (TOC), and the amount of remaining oxidizing agent is determined in a redox cell to ascertain how much of the oxidizing agent was consumed by the organic carbon. This is the COD.

9 Claims, 4 Drawing Figures

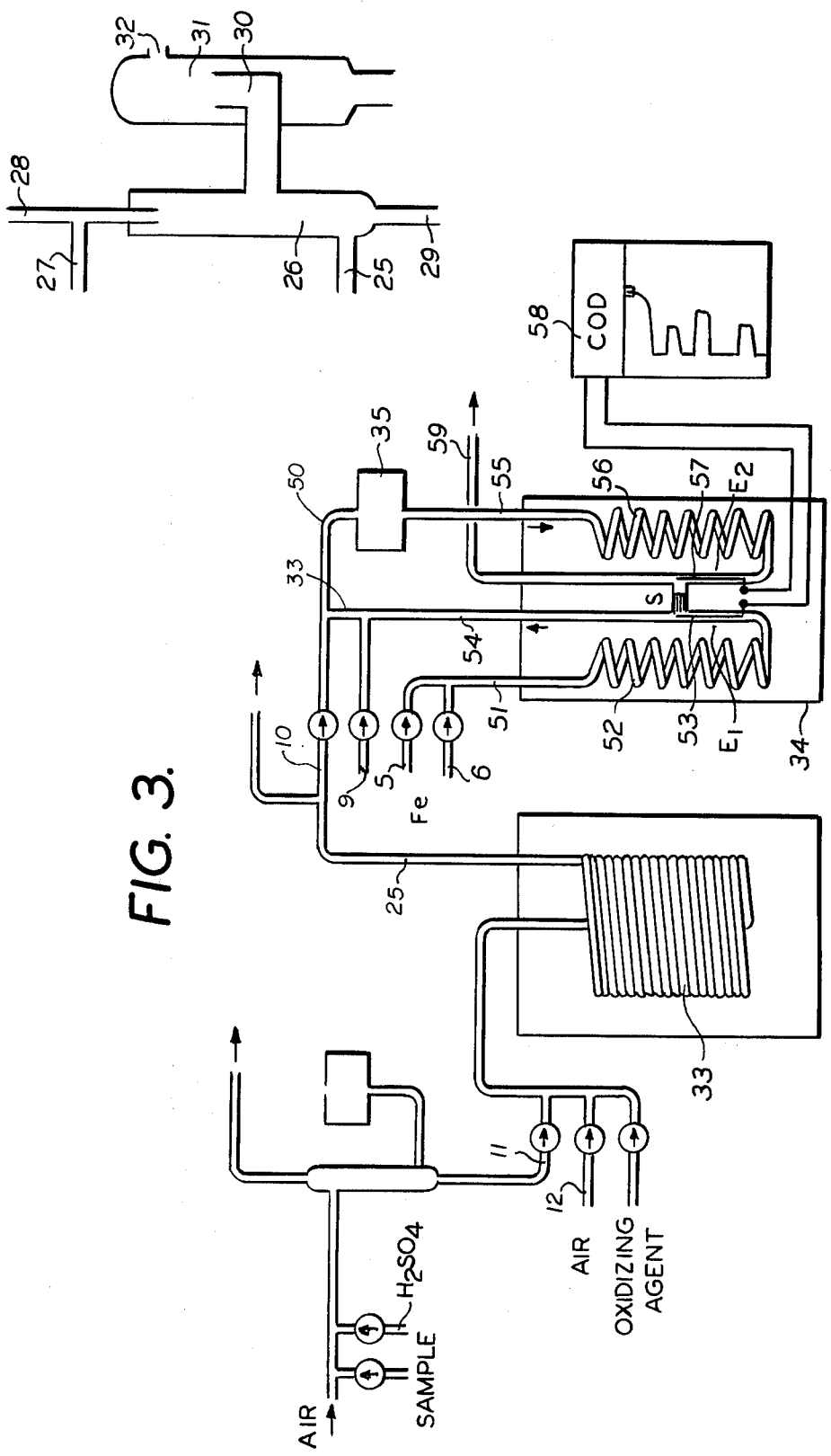

METHOD AND APPARATUS FOR TESTING AQUEOUS SAMPLES

BACKGROUND OF THE INVENTION

1. Field of the Invention

The invention relates to methods and apparatus for monitoring aqueous samples, in particular, waste waters, to determine their suitability for discharge into large bodies of water such as lakes, rivers and seas. In particular, the invention relates to methods and apparatus for determining the carbon content of such aqueous samples.

2. Description of the Prior Art

There is a known method for determining the total carbon content and the inorganic carbon content of an aqueous sample. According to this method, each of these quantities is measured difference between the two. According to this method, the organic carbon is catalytically burned to form carbon dioxide, and any inorganic carbon is thermally decomposed to form carbon dioxide.

Another known method determines the consumption of oxidizing agent by catalytic combustion, with the oxygen required for the oxidation being determined by physical chemical measurement methods.

The known methods all involve the use of relatively complicated apparatus and it is therefore an object of the present invention to provide methods and apparatus which enable one to operate continuously in a far simpler manner than has been heretofore possible.

In addition, the known methods can only be used for one determination at a time, namely, either the determination of the carbon content of the sample or the determination of the consumption of oxidizing agent. This represents a disadvantage since the ability to obtain both values simultaneously would make the results substantially greater in probative value for judging the quality of a water sample. Thus, another object of the present invention is to provide a method which can simultaneously determine the consumption of oxidizing agent and the inorganic and organic carbon content of an aqueous sample.

SUMMARY OF THE INVENTION

The present invention provides a method and apparatus for continuously determining the inorganic carbon content and the organic carbon content (TOC) of an aqueous sample and the consumption of an oxidizing agent (chemical oxygen demand — COD) by such a sample. These three data, when simultaneously available, will give a quite useful picture of the state of an aqueous sample and in particular its suitability for discharge into a body of water.

According to the invention, a stream of an aqueous sample to be analyzed is continuously subjected to treatment with a strong acid such as sulfuric acid, which converts any inorganic carbon and/or chlorides to a gas which is analyzed to determine the total inorganic carbon content. The remaining liquid is then continuously treated with an excess of an oxidizing agent at constant temperature to convert all the organic carbon contained therein to carbon dioxide. The thus produced carbon dioxide is removed from the gas-liquid mixture and is introduced to a conductivity measuring cell where the TOC is determined using a sodium hydroxide solution as the reaction medium. The excess, unreacted oxidizing agent is then determined in a redox potential measuring cell by titrating it with a redox reagent system such as a mixture of ferric and ferrous ammonium sulfate. The difference between the amount of added oxidizing agent and the unreacted oxidizing agent is a measure of how much oxidizing agent was consumed by the sample and thus gives the COD.

BRIEF DESCRIPTION OF THE DRAWING

FIG. 2 is an enlarged view of a portion of the apparatus of FIG. 1, which is the gas-liquid separator shown therein;

FIG. 3 is a schematic diagram showing the operation of the apparatus for determing COD alone;

DESCRIPTION OF THE PREFERRED EMBODIMENTS

According to the invention, a homogeneous aqueous sample to be analyzed is continuously treated with a strong acid to convert the inorganic carbon contained therein to a gas. The gas is then removed from the resulting gas-liquid mixture and the content of inorganically bound carbon is determined. The liquid portion of the mixture is then continuously treated with an excess of an oxidizing agent at a constant temperature to oxidize the organic carbon to carbon dioxide. The carbon dioxide is then removed and the TOC is determined in a conductivity measuring cell. The amount of unreacted or excess oxidizing agent is determined in a redox cell to ascertain how much oxidizing agent was consumed by the sample. This data is the COD, the determination of which is one of the objects of the invention.

The method of the invention has the advantage that all three of these values, i.e., inorganic carbon, total organic carbon (TOC) and chemical oxygen demand (COD) can be determined simultaneously. Moreover, the method makes it possible to use a continuously operating apparatus with continuous recording measurement of all three values. Since, in contrast to the methods used until now, the organic substances are digested in a wet state, a substantially larger volume of sample can be used for the analysis.

It is preferred, according to the invention, to use a mixture of potassium dichromate and silver sulfate ($Ag_2SO_4$) as the oxidizing agent, and concentrated sulfuric acid as the strong acid.

The invention will now be described in more detail with reference to the drawings.

Figure 1:
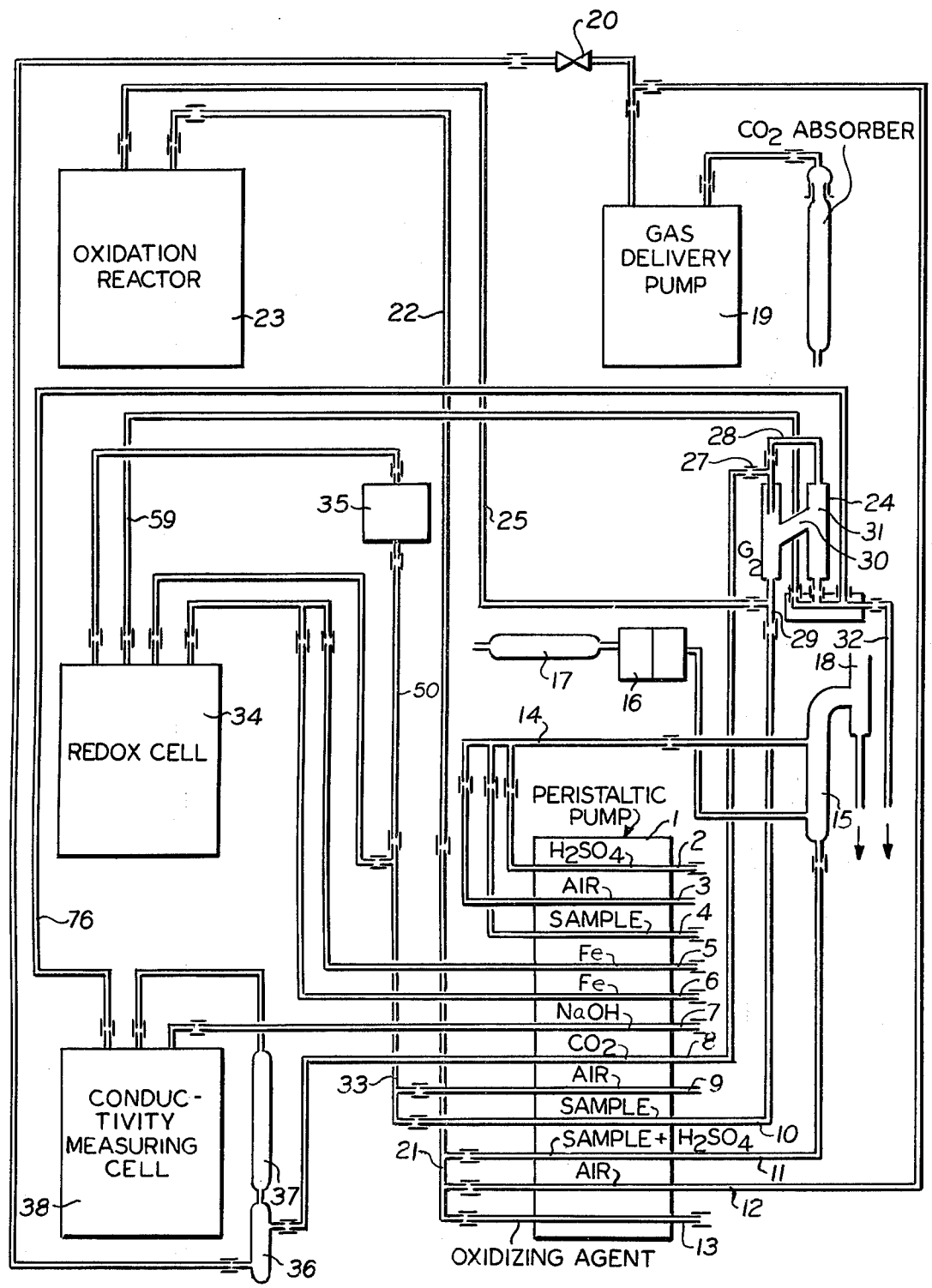
FIG. 1 is a schematic representation of apparatus according to the invention for performing the method of the invention.

As seen in FIG. 1, a multi-channel, peristaltic pump 1 is provided for introducing the sample stream and the several reactant streams in the process. A sample stream is drawn through channel 4, concentrated sulfuric acid through channel 2, and $CO_2$-free air through channel 3 of the multi-channel peristaltic pump 1 and are mixed with each other in a collector 14, where the inorganically bound carbon is converted to carbon dioxide by the action of the sulfuric acid. The resulting gas-liquid mixture passes into gas-liquid separation chamber 15, and a $CO_2$-free stream of air is blown into the lower part thereof by means of a gas pump 16 and $CO_2$ absorber 17. This stream of gas absorbs the $CO_2$ derived from the inorganically bound carbon and the stream is conducted, via outlet 18 of the gas-liquid separating chamber 15 to a conventional $CO_2$ analyzer (not shown) where the content of inorganic carbon is determined.

The remaining liquid portion of the sample is drawn, via channel 11 of pump 1, out of the separating chamber 15 and is mixed in the collector 21 with an oxidation mixture fed through channel 13 of pump 1 and consisting of potassium dichromate and silver sulfate and with $CO_2$-free air which is brought by gas delivery pump 19 and pressure valve 20 to a pressure greater than atmospheric pressure and fed through channel 12 of pump 1. This mixture is conducted through a conduit 22 into a conventional oxidation reactor 23, where the reaction takes place as the mixture flows through a helical glass tube maintained at constant temperature by a thermostatically controlled oil bath. In this reactor, the oxidation mixture reacts with the sample to convert the organic carbon to carbon dioxide which eventually is analyzed to determine the TOC. The excess of the oxidation mixture, of course, remains unreacted and will be used to determine the COD.

After passing through the oxidation reactor 23, the gas-liquid mixture passes through conduit 25 into gas-liquid separating chamber 24 which is shown in greater detail in FIG. 2. As seen in FIG. 2, the gas, which contains the $CO_2$ derived from the organic carbon, is separated from the gas-liquid mixture in riser 26 and is drawn off through outlet 27 via channel 8 of the pump 1. Pressure variations are equalized by means of vent 28.

A portion of the liquid is withdrawn from separater 24 by outlet 29 and thence, through channel 10 of the pump 1 for use in determining the consumption of oxidizing agent. The remainder of the liquid flows, via riser 30 into discharge tube 31 which is in communication with the ambient atmosphere via opening 32.

In order to determine the consumption of oxidizing agent, and thus, the COD, air is introduced via channel 9 of pump 1 into collector 33 where it mixes with the stream of liquid sample introduced via channel 10 of pump 1. At the same time, a solution of ferric and ferrous ammonium sulfate is added, via channels 5 and 6 of the pump 1, from whence it is conducted to redox cell 34. Redox cell 34 is shown in greater detail in FIG. 3 and the following description of the operation of redox cell 34 to determine the COD will be given with reference to FIG. 3.

As seen in FIG. 3, the sample, introduced via channel 10 and the air, introduced via channel 9, are mixed in collector 33 from whence it is conducted, via conduit 50 to homogenizer 35. The ferric and ferrous ammonium sulfate solution, introduced by channels 5 and 6 into redox cell 34 by means of conduit 51 pass into coiled tube 52 having electrode 53 disposed therein. The potential of this stream is measured by electrode 53 and then the sample is conducted via conduit 54 into collector 33 where it is mixed with the sample. In the homogenizer, the excess of the oxidizing agent is reacted with the ferric and ferrous ammonium sulfate, and then the mixed samples are conducted, via conduit 55 into coiled tube 56 having a second electrode 57 disposed therein. The potential of the mixed samples is measured by electrode 57 and the difference between the two potentials is recorded on recording device 58. This difference in potential is a measure of the COD. The sample, after having been analyzed, passes from the redox cell 34 via conduit 59 and thence out of the system via opening 32.

In order to determine the TOC, the $CO_2$ which is derived from the organic carbon present in the original sample is withdrawn from gas-liquid separater 24 via outlet 27 and channel 8 of the pump 1. From the pump 1, this stream is introduced to chamber 36, where it is mixed with a stream of $CO_2$-free air pumped into the system by pump 19.

The remaining description of the determination of the TOC will be given with reference to FIG. 4 which, in addition to giving a schematic diagram of the operation of the apparatus for determining TOC, also includes a representation of the simultaneous determination of the COD. This latter portion of FIG. 4 is similar to FIG. 3 which has already been described above.

Figure 4:
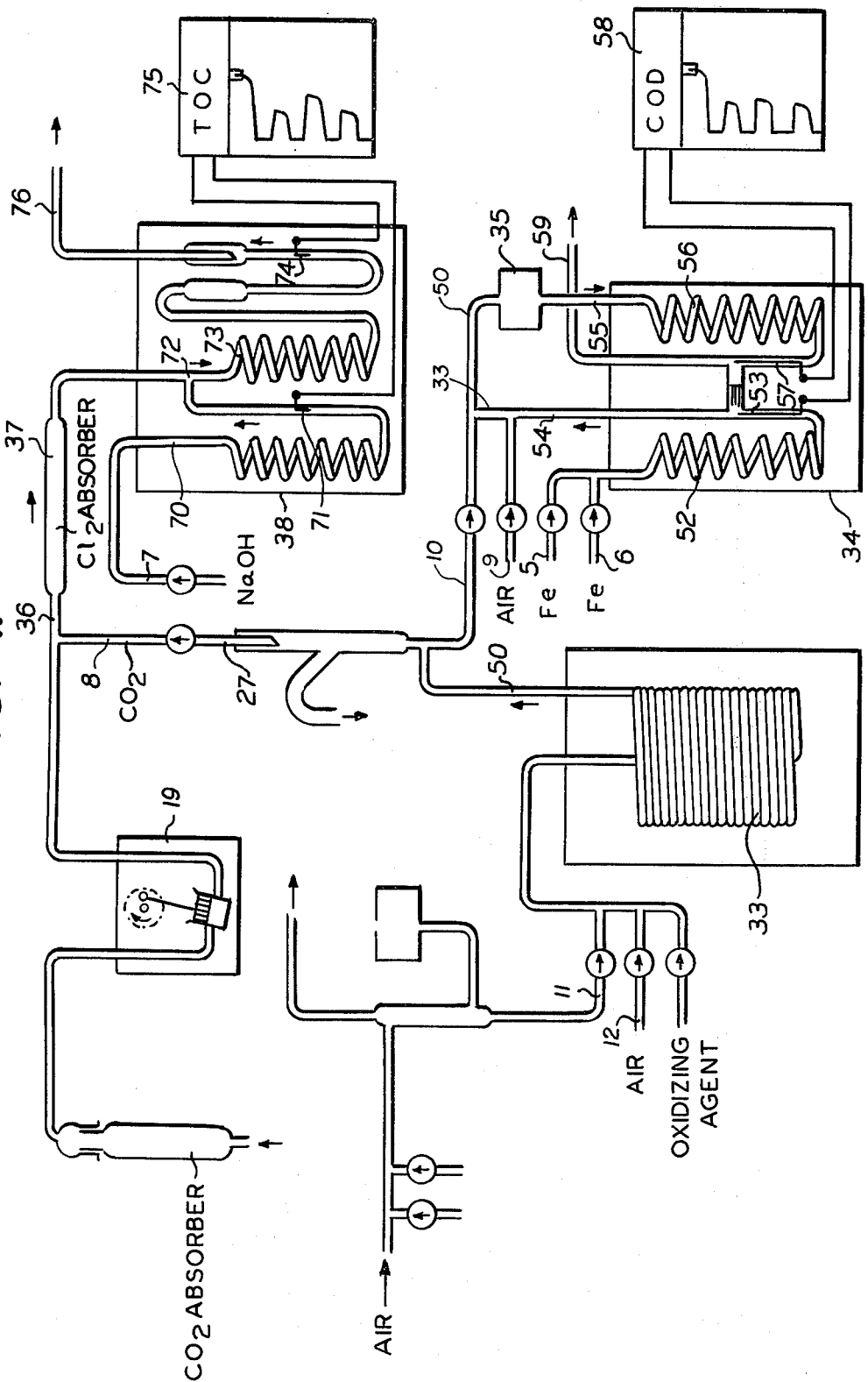
FIG. 4 is a schematic diagram showing the operation of the apparatus for determining TOC and COD together.

As seen in FIG. 4, the $CO_2$ stream is mixed with $CO_2$-free air in chamber 36, from whence it passes into chlorine absorber 37 filled with tin granulate to remove any chlorine gas which may be present in the stream of $CO_2$. The amount of $CO_2$ present in the sample is determined by the relative conductivity method against a standard NaOH solution. This NaOH solution is introduced, via channel 7 of pump 1 into tube 70 of conductivity cell 38 having a pair of electrodes 71 disposed therein. The electric conductivity of the NaOH is determined by electrodes 71. After the electric conductivity measurement is taken by electrodes 71, the NaOH is conducted to mixer 72 where it is mixed with the $CO_2$ sample coming from chlorine absorber 37. The mixture of NaOH and $CO_2$ is then conducted, via tube 73 to a second pair of electrodes 74 where the electric conductivity is again measured. The difference in the conductivity measurements is a function of the total carbon present in the sample and therefore, the TOC. The results of the electric conductivity measurements are recorded on recording device 75. The sample, after having been analyzed, passes from the system via outlet 76.

Variations can, of course, be made without departing from the spirit and scope of the invention.

Having thus described the invention, what is desired to be secured by Letters Patent and hereby claimed is:

1. A method of simultaneously and continuously determining the amount of inorganic carbon and organic carbon contained in an aqueous sample, and of determining the amount of an oxidizing agent consumed by such sample, this method comprising continuously treating a homogeneous aqueous sample with a strong acid to convert all the inorganically bound carbon contained in said sample to carbox dioxide and thereby form a first gas-liquid mixture including said formed carbon dioxide and the treated sample, separating the gas, which is carbon dioxide, from said first gas-liquid mixture and determining the amount thereof, treating the liquid portion of said first gas-liquid mixture with an excess of an oxidizing agent to thereby convert all the organically bound carbon contained therein to carbon dioxide and thus form a second gas-liquid mixture, separating the gas, which is carbon dioxide, from said second gas-liquid mixture and determining the amount thereof, said amount being a measure of the total organic carbon of said sample and measuring the amount of unreacted oxidizing agent contained in the liquid portion of said second gas-liquid mixture to thereby determine the amount of said oxidizing agent which has been consumed by the sample.

2. A method as claimed in claim 1 wherein the strong acid is concentrated sulfuric acid.

3. A method as claimed in claim 1 wherein the oxidizing agent is a mixture of potassium dichromate and silver sulfate (I).

4. A method as claimed in claim 1 wherein the amount of carbon dioxide contained in the second gas-liquid mixture is determined by conductimetrically titrating said carbon dioxide with sodium hydroxide in a conventional conductivity measuring means.

5. A method as claimed in claim 1 wherein the amount of unreacted oxidizing agent contained in the liquid portion of said second gas-liquid mixture is determined by reacting said unreacted oxidizing agent with a redox reagent having a previously determined potential and thereafter determining the potential of the reaction mixture, the difference between said two potentials being a measure of the amount of unreacted oxidizing agent.

6. A method as claimed in claim 5 wherein the redox reagent is a mixture of ferrous ammonium sulfate and ferric ammonium sulfate.

7. A method as claimed in claim 4 comprising removing chlorine gas contained in the carbon dioxide portion of the second gas-liquid mixture before said carbon dioxide is conductimetrically titrated with sodium hydroxide.

8. A method as claimed in claim 7 wherein said chlorine gas is removed by passing said carbon dioxide through a chlorine removal zone having tin granulate disposed therein.

9. Apparatus for analyzing aqueous samples comprising, in combination, a multi-channel peristaltic pump for continuously introducing measured amounts of a plurality of samples and reagents into said apparatus, reacting means connected to and operatively associated with said pump for reacting an aqueous sample with a strong acid to convert inorganically bound carbon in said sample to carbon dioxide, separating means connected to said reacting means for separating said carbon dioxide from said sample, an oxidation reactor connected to and operatively associated with the separating means, for reacting the sample, from which carbon dioxide has been removed, with an oxidizing agent to convert organically bound carbon in said sample to carbon dioxide, gas-liquid separation means for separating said carbon dioxide from the sample having the oxidizing agent added thereto, means for determining the amount of carbon dioxide obtained from said organically bound carbon, measuring means for determining the amount of oxidizing agent remaining in said sample after the separation of said carbon dioxide, and recording means for continuously recording the results of the determinations of carbon dioxide and remaining oxidizing agent, said recording means being connected to and operatively associated with said measuring means.

* * * * *

PO-1050
(5/69)

UNITED STATES PATENT OFFICE
CERTIFICATE OF CORRECTION

Patent No. 3,930,798                    Dated  January 6, 1976

Inventor(s) GUNTER SCHIERJOTT and HERBERT A. BLEIER

It is certified that error appears in the above-identified patent and that said Letters Patent are hereby corrected as shown below:

Title page, left side, the inventors: "Gunter Schierjott, Tm Haarmannsbusch 1, 463 Bochum, Germany; Herbert A. Bleier, Barawitzkagasse 27/1/536, A-1190 Vienna, Austria" should read -- Gunter Schierjott, D 463 Bochum, Im Haarmannsbusch 1, Bochum, West Germany; Herbert A. Bleier, A 1190 Vienna, Barawitzka-Gasse 27/1/5/36 Austria --.

Column 4, line 52: "carbox dioxide" should read -- carbon dioxide --.

Column 5, line 8: "determinined" should read -- determined --.

Signed and Sealed this thirteenth Day of April 1976

[SEAL]

Attest:

RUTH C. MASON
Attesting Officer

C. MARSHALL DANN
Commissioner of Patents and Trademarks